United States Patent
Ludvig et al.

(10) Patent No.: US 9,042,974 B2
(45) Date of Patent: May 26, 2015

(54) APPARATUS AND METHOD FOR MONITORING AND TREATMENT OF BRAIN DISORDERS

(75) Inventors: Nandor Ludvig, Richmond Hill, NY (US); Lorant Kovacs, Garden Grove, CA (US); Ruben Kuzniecky, Englewood, NJ (US); Orrin Devinsky, Short Hills, NJ (US); Werner Doyle, New York, NY (US); Walter Blumenfeld, Airville, PA (US); Geza Medveczky, Cortlandt Manor, NY (US)

(73) Assignee: NEW YORK UNIVERSITY, New York, NY (US)

( * ) Notice: Subject to any disclaimer, the term of this patent is extended or adjusted under 35 U.S.C. 154(b) by 1453 days.

(21) Appl. No.: 11/224,661

(22) Filed: Sep. 12, 2005

(65) Prior Publication Data
US 2007/0060973 A1    Mar. 15, 2007

(51) Int. Cl.
| | | |
|---|---|---|
| A61B 5/04 | (2006.01) | |
| A61B 5/07 | (2006.01) | |
| A61B 5/1473 | (2006.01) | |
| A61B 5/00 | (2006.01) | |
| A61B 5/0476 | (2006.01) | |
| A61B 5/145 | (2006.01) | |

(52) U.S. Cl.
CPC ............. *A61B 5/076* (2013.01); *A61B 5/04001* (2013.01); *A61B 5/0476* (2013.01); *A61B 5/14532* (2013.01); *A61B 5/14542* (2013.01); *A61B 5/14546* (2013.01); *A61B 5/1473* (2013.01); *A61B 5/4094* (2013.01); *A61B 5/4839* (2013.01)

(58) Field of Classification Search
CPC . A61N 1/0534; A61N 1/0531; A61N 1/3606; A61N 1/36025; A61N 1/36064; A61B 5/0476; A61B 5/4094
USPC .................... 600/544; 607/45; 604/891.1, 67
See application file for complete search history.

(56) References Cited

U.S. PATENT DOCUMENTS

| | | | | |
|---|---|---|---|---|
| 4,214,591 A | * | 7/1980 | Sato et al. ..................... 600/544 |
| 5,180,366 A | * | 1/1993 | Woods ....................... 604/96.01 |
| 6,038,480 A | | 3/2000 | Hrdlicka et al. |
| 6,091,979 A | | 7/2000 | Madsen |
| 6,497,699 B1 | * | 12/2002 | Ludvig et al. .............. 604/891.1 |
| 7,077,822 B1 | * | 7/2006 | Howard, III ............... 604/93.01 |

(Continued)

OTHER PUBLICATIONS

L. Kovacs, et al. "Vector-analysis: Low-power-requesting Software for Real-time Eeg Seizure Recognition/prediction in Hybrid Neuroprosthetic Devices", *Epilepsia* (in press), Presented in Neurophysiology Society Joint Annual Meeting, 2005, 1 sheet.

(Continued)

*Primary Examiner* — Michael D'Angelo
*Assistant Examiner* — Christian Jang
(74) *Attorney, Agent, or Firm* — Fay Kaplun & Marcin, LLP

(57) ABSTRACT

A method and system for treating brain disorders comprises detecting activity of a first target area of the brain via a first implanted sensor and determining the presence of target brain activity by analyzing the detected brain activity in combination with treating the user based upon the determined presence of target brain activity by supplying a first therapeutic agent to the first target area via a first implanted fluid delivery member including at least one distal opening adjacent to the first target area. In addition, the system may be used as well for testing the effectiveness of drugs.

27 Claims, 7 Drawing Sheets

(56) References Cited

U.S. PATENT DOCUMENTS

| | | | |
|---|---|---|---|
| 2003/0069541 A1* | 4/2003 | Gillis et al. | 604/164.01 |
| 2003/0171738 A1* | 9/2003 | Konieczynski et al. | 604/891.1 |
| 2004/0064086 A1* | 4/2004 | Gottlieb et al. | 604/43 |
| 2004/0215162 A1* | 10/2004 | Putz | 604/500 |

OTHER PUBLICATIONS

N. Ludvig et al. "Toward the Development of a Subdural Hybrid Neuroprothesis for the Treatment of Intractable Focal Epilepsy"; *Epilepsia* (in press), Presented in Neurophysiology Society Joint Annual Meeting, 2005, 1 sheet.

J. Ferguson, et al. "Acetylcholine Epilepsy: Relationship of Surface Concentration Chronicity of Denervation, and Focus Size"; *Exp. Neurol*, vol. 46, 1975, pp. 302-314.

Kiss et al. "Cortical Spreading Depression Augments Kynurenate Levelos and Reduces Malonate Toxicity in the Rat Cortex"; *Brain Res.*, vol. 1002, 2004, pp. 129-135.

B.E. Pfingst Auditory prostheses. In: *Neural Prostheses for the Restoration of Sensory and Motor* CRC Press, Boca Raton, FL, 2001, pp. 3-7 and 26-27.

P. Troyk "Injectable Electronic Identification, Monitoring and Stimulation Systems", . Annu. Rev. Biomed. Eng., vol. 1, 1999, pp. 177-209.

* cited by examiner

APPARATUS AND METHOD FOR MONITORING AND TREATMENT OF BRAIN DISORDERS

BACKGROUND

The present invention relates generally to systems and methods for treating brain disorders. More specifically, the present invention relates to a system and method for monitoring and responding to electrophysiological changes in the brain corresponding to disorders originating primarily in the cortex but also in other regions including the spinal cord.

As known to those skilled in the art, neural activity within the brain may be influenced through direct application of therapeutic agents to the brain. As an example, the efficacy of antiepileptic agents (e.g., pentobarbital) has been studied in animals in which seizure activity has been induced through epileptogenic agents (e.g., penicillin), revealing that localized intracerebral pentobarbital application can influence seizure activity. This is described in detail in U.S. Pat. No. 6,497,699, the entire disclosure of which is hereby expressly incorporated by reference herein.

SUMMARY OF THE INVENTION

The present invention is directed to a method of treating brain disorders comprising the steps of detecting activity of a first area of the brain via a first implanted sensor and determining the presence of target brain activity by analyzing the detected brain activity in combination with treating the user based upon the determined presence of target brain activity by supplying a first therapeutic agent to the first area via a first implanted fluid delivery member including at least one distal opening adjacent to the first area.

DETAILED DESCRIPTION

Figure 1:
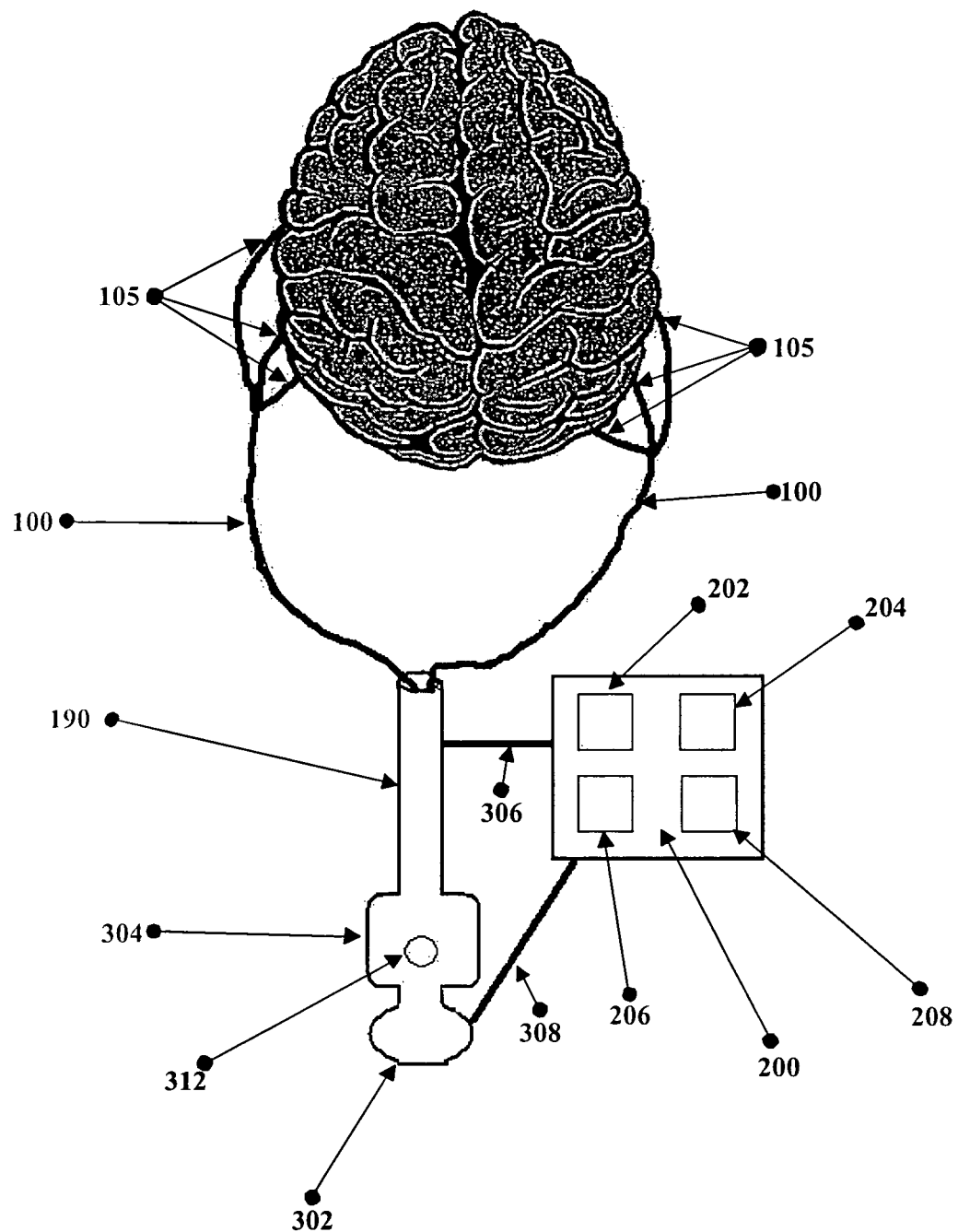
FIG. 1 shows an exemplary embodiment of a system according to the present invention.

The present invention may be further understood with reference to the following description and the related appended drawings, wherein like elements are provided with the same reference numerals. The present invention describes a system combining pharmacological and electrophysiological instruments for the treatment of brain disorders. A system in accordance with the present invention may include a sensing device and catheter implanted in the subdural space with optional additional catheters and sensory devices implanted in the ventricular system and brain tissue, a therapeutic agent reservoir and a pump unit, a signal conditioner, and a microcontroller. The present invention is also suitable for drug testing. In drug testing applications, the delivery of therapeutic agents may be automated or individually selected by, for example, remote control.

In one respect, the present invention is directed to a system and method for controlling brain activity (e.g., treating focal epileptic seizures) employing a fully implantable subdural brain activity sensing and therapeutic agent delivering member to supply therapeutic agents to selected areas of the cerebral cortex automatically upon the detection of predetermined abnormal patterns or events in the activity of the brain. The present invention provides a treatment for users for whom traditional treatments for brain disorders have been either ineffective due to, for example, inadequate response to systemically applied drugs or nonviable due to, for example, risk factors associated with surgical interventions.

Figure 2:
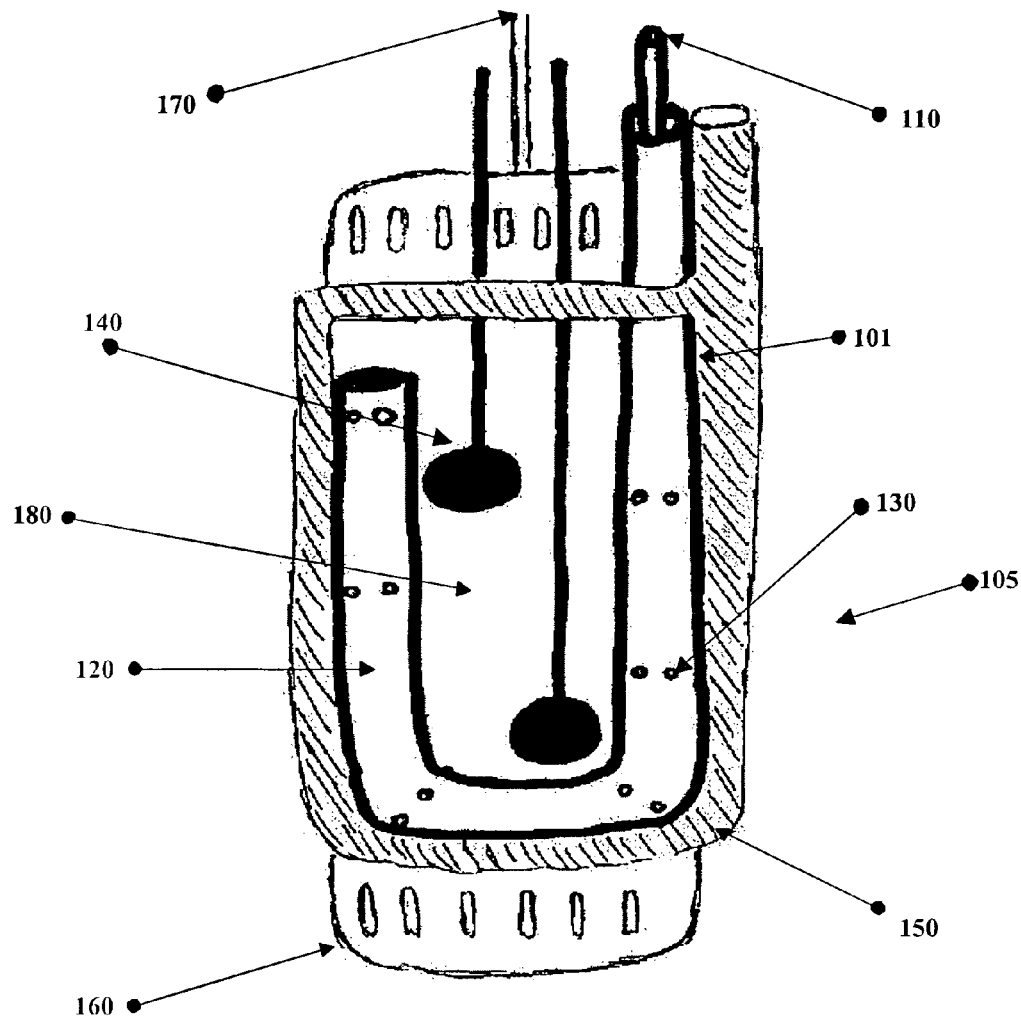
FIG. 2 shows a cross-sectional view as seen from a surface of a cerebral cortex of an exemplary embodiment of a distal end of the sensing and delivery member according to the present invention.

As shown in FIGS. 1 and 2, a system for sensing brain activity and delivering therapeutic agents to selected brain locations according to an exemplary embodiment of the present invention may include one or more sensing and delivery members 100, with each sensing and delivery member 100 including a catheter 101 defining one or more fluid lumens and one or more sensing devices 140 associated therewith. As would be understood by those skilled in the art, the catheter 101 is preferably formed of a flexible biocompatible material such as, for example, silicon. The sensing devices 140 may include, for example, an electrode for sensing electrical activity of neurons and/or neuron-populations in the brain and/or a neurochemical sensor for detecting chemical activity (e.g., glutamate release) or a chemical state (e.g., extracellular glucose level) of an area of the brain or any other sensing device capable of detecting data corresponding to activity of a selected area of the brain (e.g., blood flow). The system further includes a control unit 200, a shielding tube 190, a pump 302, and a reservoir system 304. The control unit 200 communicates with each sensing device 140 of each sensing and delivery member 100 via a bus 306 connected to a signal conditioner 202, and is also connected to the pump 302 via a bus 308. As will be described in more detail below, in use, the distal end of each sensing and delivery member 100 (i.e., the end of each sensing and delivery member 100 distal to the control unit 200) is positioned adjacent to a targeted area of the brain to sense activity in that area and to deliver therapeutic agents thereto in response to the sensed activity. Those skilled in the art will understand that, although the exemplary sensing and delivery member 100 described herein includes a separate catheter 101 and sensing device 140, any number of arrangements of these elements is possible. For example, some or all of the sensing device 140 may be embedded within a corresponding catheter 101, or some or all of the sensing device 140 may be otherwise coupled to the corresponding catheter 101 by, for example, being wound about or tied to the catheter 101. In addition, one or more sensing devices 140 may be provided without a corresponding catheter 101 and vice versa. That is, depending on the particular characteristics of a person in whom the system is to be implanted, it may be desirable to monitor the activity of certain areas of the brain without applying any therapeutic fluids thereto. A sensing device 140 without a corresponding catheter 101 may be positioned in each of these areas. Alternatively, there may be one or more areas of the brain to which it is desired to supply fluids without regard to the activity therein. Thus, a catheter 101 not including a sensing device 140 may be positioned in each of these areas.

FIG. 2 shows a preferred embodiment of an integrated subdural unit 105, which receives a distal end of one of the sensing and delivery members 100 (e.g., a distal end of a catheter 101 and a distal, sensing end of the sensing device 140 of the catheter 101). Each integrated subdural unit 105 is mounted adjacent to a target area of the brain with a sealing membrane 150 thereof surrounding a distal active area 180 of the corresponding catheter 101 and sealingly contacting an inner surface of the dura mater/arachnoid and the outer surface of the cerebral cortex to permit interaction only with the portion of the cerebral cortex circumscribed by the sealing membrane 150 and only that portion of the brain circumscribed by the sealing membrane 150. The sealing membrane 150 is preferably expandable so that a sealing pressure applied by a dorsal segment of the sealing membrane 150 to the arachnoid/dura mater and, by a ventral segment of the sealing membrane 150 to the underlying pia mater/cerebral cortex may be controlled to a desired level. For example, the sealing membrane 150 may be inflatable (e.g., through the supply of a fluid such as, for example, articifical or natural cerebrospinal fluid or saline). Such an inflatable sealing membrane 150 may optionally be coupled to the pump 302, or a separate dedicated pump (not shown), via an inflation lumen (not shown) so that the inflation level may be varied to maintain the desired sealing pressure or to vary the sealing pressure over time. However, alternate embodiments are possible where, for example, the sealing member 150 is formed of a compliant material which may, for example, be any compressible, biocompatible material such as a memory foam or cohesive silicone gel. Furthermore, depending on the degree of sealing of the active area desired, the material may be selected to be completely non-porous or may be absorbent, etc.

The catheter 101 according to the exemplary embodiment of the invention includes an inner tube 110 received within a fluid lumen of an outer tube 120 with a plurality of perforations 130 being formed through an outer wall of the outer tube 120 only in the active area 180. The fluid lumen of the outer tube 120 preferably serves as a conduit for the delivery of a therapeutic agent to the active area 180 while the lumen of the inner tube 110 preferably serves as a conduit for the intermittent delivery of artificial or natural cerebrospinal fluid or saline to the distal end of the catheter 101 to flush the perforations 130 and prevent clogging. Alternatively, the outer tube 120 may be used for fluid intake from the active area 180 while the lumen of the inner tube 110 may serve as a fluid outlet thereto. In addition, each of the inner and outer tubes 110, 120, respectively, may be used to deliver a different therapeutic agent to the active area 180. The perforations 130 may preferably have a diameter of between 5 and 20 micrometers.

The perforations 130 may, for example, be formed by laser pulses, but may alternatively be formed by mechanical means such as piercing or cutting. The perforations 130 are preferably of sufficient diameter to permit the free passage of fluid and/or therapeutic agents between the outer tube 120 and the active area 180 without exerting substantial pressure on the walls of the outer tube 120 and without restricting the passage of such therapeutic agents as large molecules including, for example, proteins. The perforations 130 are preferably sufficiently small to exclude the entry of brain cells and tissue debris into the lumens of the inner and outer tubes 110, 120, respectively. This further reduces the likelihood of clogging of the perforations 130. However, the perforations 130 should be sufficiently large so that the pressures which must be applied to the fluid supplied to the outer tube 120 to obtain desired flow rates will not compromise the structural integrity of the outer tube 120 or cause discomfort or injury. The inner tube 110 is in fluid communication with the active area 180 via an opening of its lumen at a distal end of the inner tube 110 either via a single opening underlying the initial zone of perforations 130 or via multiple holes underlying the entire area of perforations 130. As would be understood by those skilled in the art, the geometric shape and internal arrangement of the integrated subdural unit 105 may vary depending on its intended use and intended site of implantation. For example, an integrated subdural unit 105 may be substantially disc-shaped with a distal portion of an outer tube 120 thereof formed substantially in the shape of a disc having the perforations 130 spread across its entire surface and with the inner tube 110 running within a lumen of this disc while the sensor 140 is attached to an outer wall of the integrated subdural unit 105.

Also received within the integrated subdural unit 105 is at least one sensing device 140, an anchoring membrane 160 and, optionally, a guidewire 170 removably received along an outer wall or predefined channel of the sensing and delivery member 100. As would be understood by those skilled in the art, the anchoring membrane 160 is preferably formed of a biocompatible material that facilitates the in-growth of connective tissue such as, for example, a textured polymer or elastomer. The function of the anchoring membrane 160 is to prevent undesirable displacement, floating, or other movement of the integrated subdural unit 105 after implantation over a target cerebral cortical area.

Those skilled in the art will understand that employing a single, dual-lumen catheter 101 in place of separate catheters for intake and outflow (or for the supply of different fluids) makes more efficient use of space which may be of paramount importance in such applications. However, if desired, separate catheters may be used in place of the dual-lumen catheter 101. Alternatively, a single, single lumen catheter may be substituted for the catheter 101 for a system in which only a single therapeutic fluid is to be supplied. In addition, the proximal end of such a single lumen catheter may separate into branches connected to, for example, separate therapeutic fluid reservoirs, a drained fluid receptacle, etc. to allow such a system to perform functions which might otherwise be associated with multi-lumen or multiple catheter systems.

Incorporating the sensing device 140 into the structure of the catheter 101 further reduces the space required for the device. However, if desired, a sensing device 140 completely separate from the catheter 101 may also be used. Additionally, the sensing device 140 need not be limited to the active area 180. For example, a microassay of cerebrospinal or interstitial fluid removed from the active area 180 may be done by a sensing device 140 located outside the vicinity of the active area 180, along the sensing and delivery member 100 or at any other location in the body such as a location of a drainage reservoir to which such fluids are removed. Those skilled in the art will recognize that, as the number of integrated subdural units 105 at different areas of the brain increases, so do the above-noted space-saving benefits.

As shown in FIG. 1, the proximal end of the system includes a pump 302 coupled to a reservoir 304. In the exemplary embodiment, the pump 302 is an electrically controlled micro-mechanical pump. Specifically, the pump 302 may be a miniature, dual peristaltic pump allowing the alternating delivery of either a therapeutic agent, artificial or natural cerbrospinal fluid or saline, etc. via the catheters 101. In other embodiments, the pump 302 may be a piezoelectric pump, osmotic pump, an electromagnetic pump or other electrically controllable device for supplying fluid to the sensing and delivery members 100. The reservoir 304 may, for example, be a multi-chambered storage device implanted subcutaneously and may contain separate chambers for the storage of multiple fluids. This permits the pump 302 to alternately deliver the therapeutic agent and the saline or cerebrospinal fluid via the sensing and delivery members 100. Of course, those skilled in the art will recognize that the reservoir 304 may be a single chambered reservoir for holding a single therapeutic fluid. The reservoir 304 may also be constructed for implantation with at least an accessible portion 312 thereof accessible through the skin allowing for refilling of the reservoir 304 through the skin. In one embodiment, the accessible portion 312 is formed of a self-sealing polymer, capable of retaining an airtight seal even after numerous penetrations by a syringe or other access device. The accessible portion 312 provides access to the individual fluid chambers, and is preferably constructed so as to be easily distinguishable from the remaining portion of the reservoir 304. This may be accomplished by constructing the accessible portion 312 with a raised ridge or other textured, tactile, or visibly identifiable surface. If separate access to multiple chambers is required, as in the case of the dual pump 302, additional accessible portions 312 or an accessible portion with demarcated portions clearly defined for accessing each of the various chambers may be provided. As would be understood by those skilled in the art, multiple accessible portions 312 may be distinguished from one another, for example, by including varying texture patterns or ridges of varying elevations.

It will be appreciated that both the reservoir 304 and the pump 302 may be implanted at any of a variety of locations throughout the body. Those skilled in the art will recognize that there are many possible configurations for the reservoir 304 and the pump 302 which will be suitable for a system according to the invention. In other embodiments, the reservoir 304 and the pump 302 may be located outside the body. In yet other embodiments, the reservoir 304 may include a plurality of reservoirs, each coupled to a separate pump or each selectively coupled to one or more pumps.

A proximal end of the catheter 101 is coupled to a distal end of the reservoir 304, with the inner tube 110 and the outer tube 120 opening to separate chambers of the reservoir 304, thus allowing the fluids stored in the chambers to be selectively passed from a proximal to a distal end of a respective one of the tubes 110, 120 or allowing a fluid to be withdrawn from the distal end of one of the tubes 110, 120 for collection in one of the chambers while a further fluid is supplied to the distal end of the other of the tubes 110, 120 from a second one of the chambers. The proximal end of the sensing and delivery member 100 is preferably enclosed within a shielding tube 190 to protect against an exchange of fluids between the catheter 101 and an area in which it is implanted if a leak were to develop in the proximal end of the sensing and delivery member 100. In addition, the shielding tube 190 provides a convenient structure for managing a plurality of sensing and delivery members 100. By enclosing a plurality of sensing and delivery members 100 in close proximity to one another, the shielding tube 190 minimizes the amount of space required for the sensing and delivery members 100.

The control unit 200 includes, for example, a signal conditioner 202, a microcontroller 204, a power supply unit 206, and a telemetry unit 208. The signal conditioner 202 is coupled to the sensing devices 140 of the sensing and delivery members 100 for the receipt of input therefrom via the bus 306. The received signals (e.g., analog electrophysiological signals from a neuron-population) are then conditioned by the signal conditioner 202, which, for example, filters, amplifies, and converts the signal to a new form (e.g., analog-to-digital). The resulting signal is then transmitted to the microcontroller 204. However, the step of converting the analog signals to digital signals as well as the signal conditioning can be performed by the microcontroller 204 itself if, for example, the microcontroller 204 is a processor with a built in amplifier, filter and analog to digital converter.

The microcontroller 204 preferably includes one or more of a digital signal processor (DSP), a programmable logic array (PLA), an application-specific integrated circuit (ASIC), and a field-programmable gate array (FPGA) for analyzing in real-time signals received from the signal conditioner 202 to determine the presence of abnormal brain activity associated with brain disorders (or with a specific brain disorder) or to detect the onset of specific brain dysfunctions. Of course, those skilled in the art will understand that any number of other devices may be suitable to perform the functions of the microcontroller 204. Based on the results of this determination, the microcontroller 204 operates the pump 302 to treat the detected condition by the application of therapeutic fluids to and/or the removal of fluids from selected target areas of the brain at which integrated subdural units 105 have been mounted. Signal transfer between the microcontroller 204 and each of the sensing devices 140 and between the microcontroller 204 and the pump 302 is accomplished via the buses 306 and 308, respectively. Furthermore, the microcrontroller 204 may: maintain regular deliveries of cleansing fluid through the catheters 101; control an inflation state of the sealing membrane 150; and control functions of the power supply unit 206 and the telemetry system 208. In addition, among other functions, the microcontroller 204 may transfer data such as EEG signals, status information, and receive and pass on remote commands such as, for example, pump activation commands. Optionally, it may be desirable to allow the patient to assume control of the system under certain conditions. For example, if the patient feels a seizure coming on that has not been detected by the system, he may transmit a signal to the microcontroller 204 ordering immediate delivery of a dosage of a therapeutic fluid to a target area of the brain. Alternatively, the patient's indication that symptoms are present (e.g., a seizure is coming on) may be used by the microcontroller 204 to learn patient-specific EEG patterns that may be used to improve the system's ability to detect the brain activity corresponding to the symptom.

The power supply unit 206 is preferably subcutaneously disposed, along with the entire control unit 200 and is preferably transcutaneously rechargeable to power the control unit 200 and the pump 302 for an extended period of time without being physically accessed or replaced. Of course, non-rechargeable power sources may be used. However, replacement of such power sources necessitates a new surgical procedure. In one embodiment, the power supply unit 206 includes a principal power source in the form of a rechargeable battery and one or more backup batteries. As would be understood by those skilled in the art, such batteries may be transcutaneously recharged by known electromagnetic or optical means. In other embodiments, the power supply unit 206 contains a power generator, which harnesses energy by thermal, mechanical, or electrochemical means, or by a combination thereof. Exemplary transcutaneously rechargeable power supply utilizing a non-contact, inductive link (transcutaneous magnetic coupling) to transfer power from an external transmitter coil to an internal (receiver) coils are described in Troyk, P. R. (1999), Injectable Electronic Identification, Monitoring and Stimulation Systems, *Annual Rev. Biomed. Eng.;* and Pfingst, B. E. (2000), Auditory Prostheses, In: *Neural Prostheses for the Restoration of Sensory and Motor Function* (eds. Chapin, J. K and Moxon, K.), CRC Press, Boca Raton, Fla., pp. 3-43.

In an exemplary embodiment, the transcutaneously transferred energy is applied to a battery component of the power supply 206 through, for example, a Lithium ion fast charge battery management integrated circuit and a current limiting MOSFET transistor, with a switching mode charger to minimize power dissipation. Of course, those skilled in the art will understand that a wide variety of alternative power supply arrangements may be employed.

The telemetry unit 208 provides two-way communication between the microcontroller 204 and external devices, allowing for external monitoring of the user and the system and may provide for manual control of the pump 302 and other system components. External monitoring of the user may be accomplished via the collection and analysis of data on seizure frequency. As would be understood by those skilled in the art, external monitoring of the system may be accomplished via a telemetry transceiver carried by the user allowing, for example, the generation of alarm or other signals. Manual control of the system components may include, for example, post-implantation adjustment of the system software. The telemetry unit 208 preferably operates on a radio-frequency ("RF") band that minimizes interference from commonly used RF devices such as cellular phones, wireless modems and routers, and other similar devices. As would be understood by those skilled in the art, data transmissions between the telemetry unit 208 and microcontroller 204 may be encrypted to safeguard against unauthorized or unintended access to the system.

Those skilled in the art will recognize that the individual components of the system, including the control unit 200, may be located subcutaneously at any of a variety of locations throughout the body. However, in alternative embodiments of the invention, the control unit may be placed external to the body, with a wireless connection to the subcutaneous components of the system, allowing for ad-hoc reprogramming, quick repairs, etc.

Figure 3:
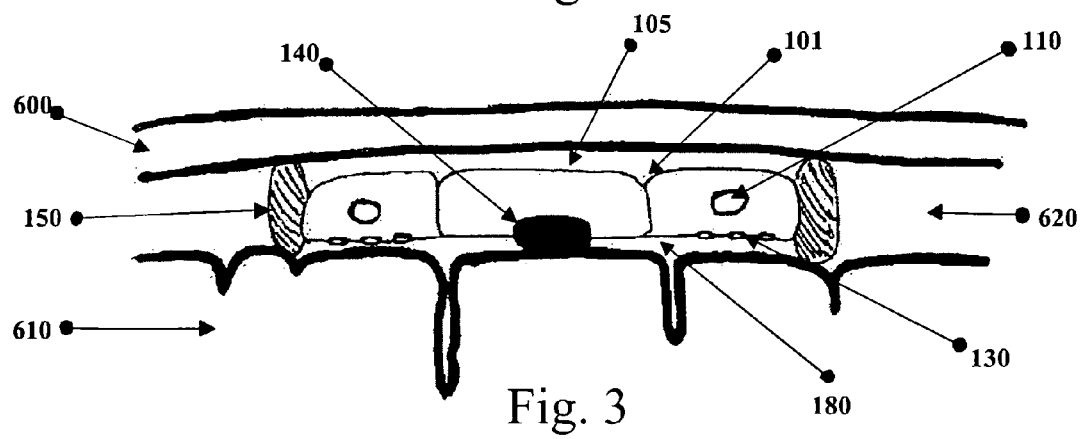
FIG. 3 shows the distal end of the sensing and delivery member implanted within a subdural cavity.

FIG. 3 illustrates a preferred embodiment of the sensing and delivery member 100 when in an operative position. In use, an integrated subdural unit 105 with a distal end of a sensing and delivery member 100 received therein is implanted at a desired location in the subdural/subarachnoid space 620 between the skull 600 and the cerebral cortex 610 of a user. The sensing device 140 is then placed in direct contact with the brain or at a desired location relative thereto, and the catheter 101 is positioned so that the perforations 130 are facing the underlying brain. Following implantation of the attachment arrangement, the sealing membrane 150 is inflated, compressed, or otherwise modified to generate the desired sealing pressure around the active area 180. As described above, the sealing membrane 150 surrounds the integrated subdural unit 105 to prevent the exchange of fluids between the active area 180 and regions of the cerebral cortex 610 lying outside the active area 180. This confines therapeutic agent delivery to the target areas of the brain and ensures that any fluids removed from the active area or analyzed therein reflect conditions within the active area 180. The anchoring membrane may then be secured in place by suturing, embedding within, or otherwise contacting nearby tissue. If desired, the entire distal end may be repositioned or removed entirely by deflating, further compressing, or otherwise modifying the sealing membrane 150 and allowing access to the active area 180. If tissue ingrowth into the anchoring membrane 160 has progressed to an undesired level preventing the catheters 101 and the sensing devices 140 from functioning properly, the ingrown tissue may be cut away from the anchoring membrane 160 depending on the degree of ingrowth and whether the subdural integrated unit 105 is to be removed or repositioned.

The remaining, non-subdural components of the system, including the pump 302, the reservoir 304, the controller 200 and the buses 306 and 308, other electrical components, etc. are then implanted in selected areas of the skull and body and the various components of the system are attached to one another via subcutaneous tunneling. The proximal ends of the sensing and delivery members 100 are attached to the reservoir 304 by, for example, inserting a proximal end of a selected one of the tubes 110 and 120 through an access hole leading to a chamber of the reservoir 304 containing a therapeutic fluid to be supplied via the selected one of the tubes 110, 120. Those skilled in the art will understand that the temporal order and spatial arrangement in which the remaining non-subdural components of the system are implanted and coupled to one another is unimportant to the functioning of the system and the described order of the steps in an implantation procedure may be varied in any manner without departing from the scope of the invention.

The shielding tube 190 is fitted over the proximal ends of the sensing and delivery members 100 with an inner diameter of the shielding tube 190 preferably chosen to match the combined diameters of the sensing and delivery members 100 to be received therein. In another embodiment, the shielding tube 190 may be formed as a sheet wrapped around the sensing and delivery members 100 so that the shielding tube 190 may be adapted for use with any number of sensing and delivery members 100. Access to a proximal end of the sensing devices 140 may be provided by, for example, an opening in the shielding tube 190 which may be formed at a distal or a proximal end of the thereof or may be defined anywhere along a length of the shielding tube 190.

The pump 302 is attached to the reservoir 304. Those skilled in the art will recognize many potential locations for placement of the components of the system. For example, the pump 302 and the reservoir 304 may be placed beneath an opening between the skin and muscle tissue at the back of the neck. Alternatively, the pump 302 and the reservoir 304 may be located in the chest or the upper or lower back, or any other suitable location with the accessible portion 312 facing the skin. It may be advantageous to locate the pump 302 and the reservoir 304 in different physical locations, for example, when the volume of the reservoir 304 is large.

The buses 306 and 308 are coupled to the sensing devices 140, the pump 302 and the control unit 200 (e.g., via an attachment port thereof). Of course, one or both ends of the buses 306 and 308 may be pre-attached to the respective components before they are implanted. The control unit 200 and the busses 306, 308 are placed subcutaneously in a manner similar to the pump 302 and the reservoir 304 and are preferably located near these components. In another embodiment, the control unit 200 remains external to the body (e.g., worn around a neck, placed in a clothing pocket, etc.) with proximal ends of the buses 306 and 308 attached to a wireless transceiver which is in wireless communication with the control unit 200. After all the components have been attached to one another and placed inside the body, the components are anchored in place (e.g., by attachment to surrounding tissue via sutures or other means) before closing the openings through which the system was implanted are closed.

Figure 4:
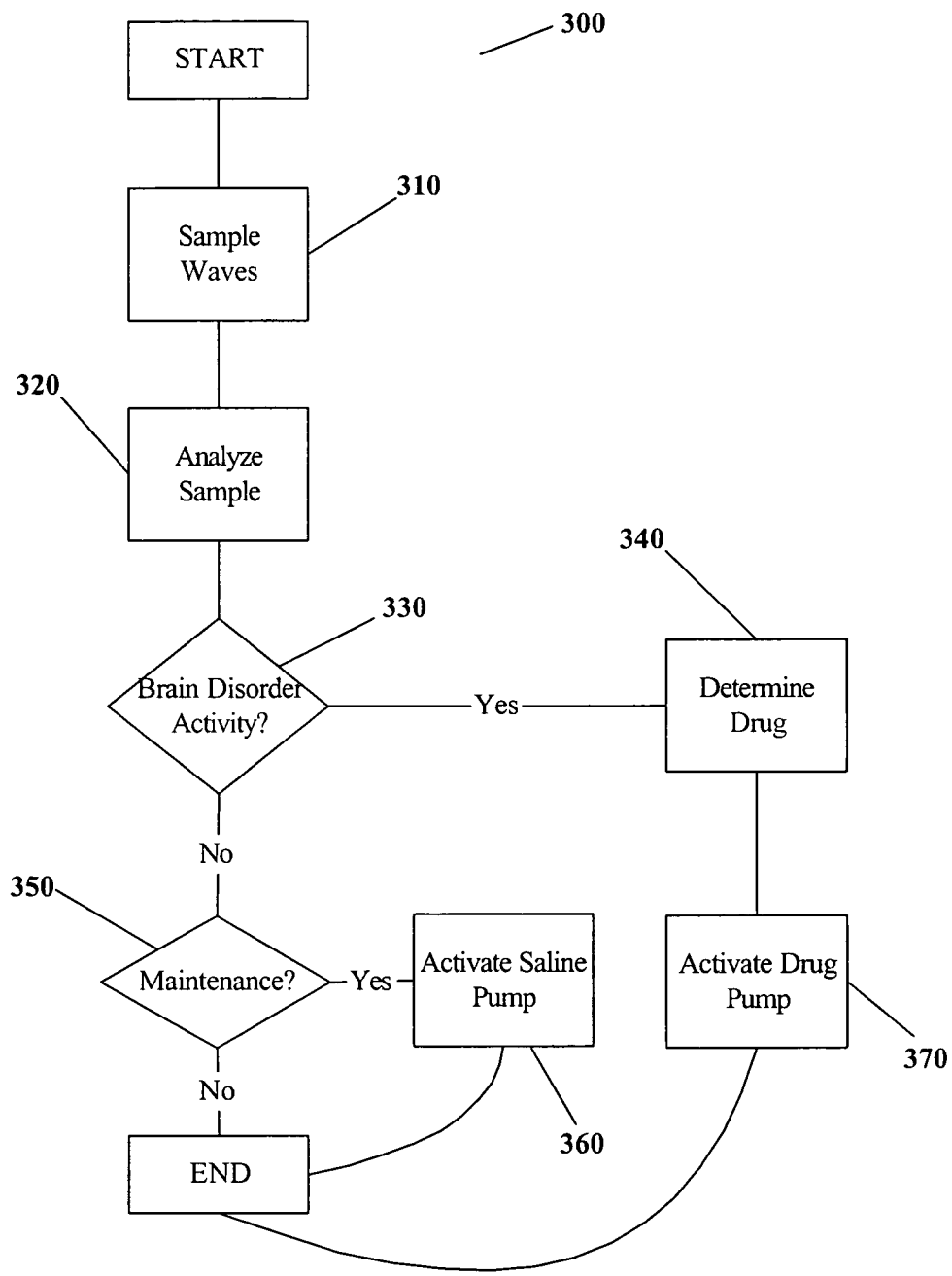
FIG. 4 shows an exemplary embodiment of a method for monitoring and treating brain activity according to the present invention.

FIG. 4 summarizes an exemplary method 300 for the monitoring and treatment of abnormal brain function (e.g., seizure generation) in accordance with the present invention. Data acquired by the sensing device 140 is sent to the control unit 200 via the bus 306 where it is conditioned by the signal conditioner (e.g., by filtering, amplifying, and converting the signal to a digital form). This conditioned signal is then forwarded to the microcontroller 204 where it may, for example, be sampled at a rate sufficient to detect specific types of brain activity (e.g., seizure or pre-seizure activity) (step 310). Those skilled in the art will understand that the sampling rate may be predetermined or adjusted based, for example, on the electrophysiological or neurochemical nature of the conditioned signals or the type of abnormal activity sought, etc. The sampling rate may also be determined based on a number of channels via which the signals are collected and based on an amplitude of and frequency range of the electrical or neurochemical waves processed for analysis in the control unit 200. The sampling rate and other signal collection parameters such as, for example, amplification and filter settings are preferably pre-programmed into the microcontroller 204 prior to implantation. However, for each patient these pre-programmed parameters may be modified and adjusted prior to implantation based, for example, on an initial data sampling from the patient. Moreover, the sampling rate and other signal collection parameters may be further modified and adjusted after implantation should this be necessary. Such post-implantation adjustment may be achieved using the telemetry system 208 as would be understood by those skilled in the art. The samples are then analyzed (step 320) in order to determine if target abnormal brain activity is occurring (step 330). For example, normative data corresponding to the activity of selected portions of the brains of individuals who exhibited symptoms of a specific brain disorder (e.g., norms determined from comparisons of a population of individuals suffering from a disorder to control data) may be compared to the activity in the corresponding portions of the brain of the patient to determine whether the detected activity indicates the presence of the disorder or specific brain dysfunctional brain activity associated with that disorder. An alternate method for detecting targeted abnormal activity is described below in reference to FIG. 5.

As described above, dysfunctional activity may be preceded by unique patterns of activity in selected portions of the brain. To monitor and treat such a dysfunction, an integrated subdural unit 105 will preferably be implanted adjacent to each of these selected portions of the brain so that data gathered from the sensing devices 140 may, for example, be compared to normative data corresponding to activity in the same regions of others who have exhibited the dysfunction. Thus, when activity analyzed by the controller 200 evidences a correlation to the normative data evidencing the unique patterns preceding the target abnormal brain activity, the microcontroller 204 consults internal software to determine the appropriate response to the detected activity. Where activity is detected which the normative data indicates is predictive of the imminent onset of the dysfunction, the microcontroller 204 may instruct the pump 302 to supply therapeutic agents to one of more of the active areas 180 to forestall the dysfunction.

The software may indicate that, upon detection of a first type of dysfunctional brain activity in an area of the brain, the microcontroller 204 operates the telemetry system 208 to generate a warning signal instructing the user to take a specific course of action (e.g., take an oral medication, seek immediate medical attention, etc.). Detection of a second type of dysfunctional brain activity may cause the software to subject the signals of this channel, as well as those of other recording channels, to further tests. Detection of a third type of dysfunctional brain activity may cause the microcontroller 204 to control the pump 302 to supply one or more therapeutic agents from the reservoir 304 to one or more of the tubes 110, 120 of the catheters 101 to treat the corresponding area(s) of the brain (step 370). When target abnormal brain activity is not detected, the microcontroller 204 determines whether a maintenance step is required (step 350), and if maintenance is required, the microcontroller 304 controls the system to perform the required maintenance. For example, the required maintenance may include the clearing of the perforations 130 in the active areas of one or more of the catheters 101 by activating the pump 302 (step 360) to deliver a flushing fluid (e.g., saline, cerebrospinal fluid or other cleansing fluid) to the active area(s) 180 of selected ones of the catheters 101. Alternatively, the microcontroller 204 may operate the telemetry system 208 to generate a warning letting the user know that other maintenance is required (e.g., charging the battery) or disable the pump 302 until the maintenance has been successfully performed. Those skilled in the art will understand that numerous additional types of maintenance may be indicated.

When the microcontroller 204 recognizes the signals as corresponding to target brain activity which indicates the delivery of one or more therapeutic agents to the brain, the system is controlled to activate the pump 302 by, for example, sending electrical signals thereto via the bus 308. For example, if a continuous drug delivery is indicated, the microcontroller 204 may generate an electrical signal continuous for a predetermined amount of time. If intermittent deliveries are indicated, the microcontroller 204 may periodically send the electrical signals to the pump 302. After the electrical signal is received therein, the pump 302 causes a therapeutic agent stored in an indicated chamber of the reservoir 304 to travel distally from the reservoir 304 through the catheter(s) 101 until the therapeutic agent exits the distal end of the selected one of the tubes 110, 120 to contact the targeted area of the brain. The sealing membrane 150 maintains the therapeutic agent within the active area 180 until it has been completely absorbed by an underlying brain tissue. However, those skilled in the art will understand that, if the sealing membrane 150 is porous, some of the therapeutic agent may flow to areas of the brain surrounding the active area 180. In some embodiments, fluid may be withdrawn through the catheter 101 to a reservoir at preselected times (e.g., for chemical analysis) or after a therapeutic agent has been present in the active area 180 for a predetermined amount of time or when the microcontroller 204 determines that the target abnormal brain activity has stopped. Once the effects of the therapeutic agent have been realized and termination of the target abnormal brain activity has been detected by the microcontroller 204, the resulting signals are analyzed by the microcontroller 204, which recognizes the cessation of the target abnormal brain activity, and ceases sending operational signals to the pump 302 to cut off the supply of thereapeutic agents.

In the exemplary system according to the present invention, the activation of the pump 302 causes a therapeutic agent stored in the reservoir 304 to be delivered to the distal end of one or more of the sensing and delivery members 100. As described above, if greater control over the delivery of the therapeutic agents is desired, the system may be configured to deliver various therapeutic agents to select branches of individual sensing and delivery members 100 or to different catheters 101. Those skilled in the art will recognize that there are many ways in which to accomplish the delivery. For example, a plurality of reservoirs 304 and pumps 302 may be used in conjunction with a plurality of sensing and delivery members 100. In other embodiments, proximal ends of the sensing and delivery members 100 may contain valves or other control mechanisms operated by the microcontroller 204.

In an alternative embodiment, the maintenance procedure may be initiated by a sensor such as, for example, a pressure sensor or a strain gauge located at the distal end of the catheter 101 so that substantial pressure on the walls of the distal end of the catheter 101 resulting from an attempt to deliver a therapeutic agent through clogged perforations 130 triggers the release of the cleansing fluid. The sensor may also be used to monitor the maintenance procedure. For example, the sensing device may communicate to the microcontroller 204 when the perforations 130 have been sufficiently cleared, or if the maintenance procedure has been unsuccessful, the sensor may alert the microcontroller 204 that the perforations 130 remain clogged. Other embodiments may have scheduled flushings at predetermined intervals.

Although the system according to the present invention is designed to be self-maintaining, a manual maintenance procedure may occasionally be required. Such maintenance may include the recharging and/or replacement of the power supply unit 206, reprogramming of the control unit 200, or more commonly, a refilling or emptying of one or more chambers of the reservoir 304. In the exemplary embodiment, the reservoir 304 may be refilled or emptied through the skin by piercing the accessible portion 312 with a syringe or other access device. Fluid may then either be introduced to or withdrawn from the chamber of the reservoir 304 corresponding to the accessible portion 312 pierced by the access device. In an alternative embodiment, the reservoir may be located external to the body of the user, and may be refilled through a predefined opening accessible through a sealing mechanism such as a cap or a valve.

Figure 5:
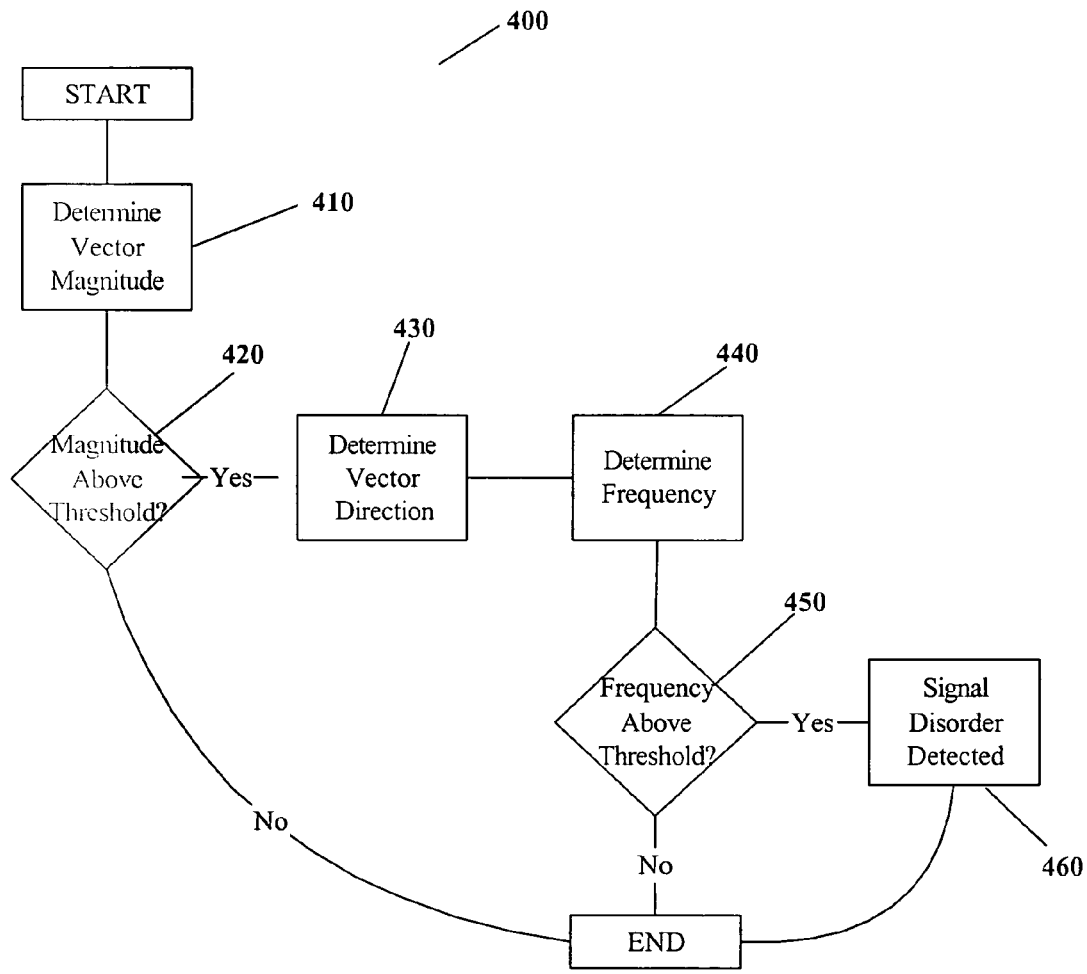
FIG. 5 shows an exemplary embodiment of a method for the detection of a target brain activity according to the present invention.
Figure 7A:
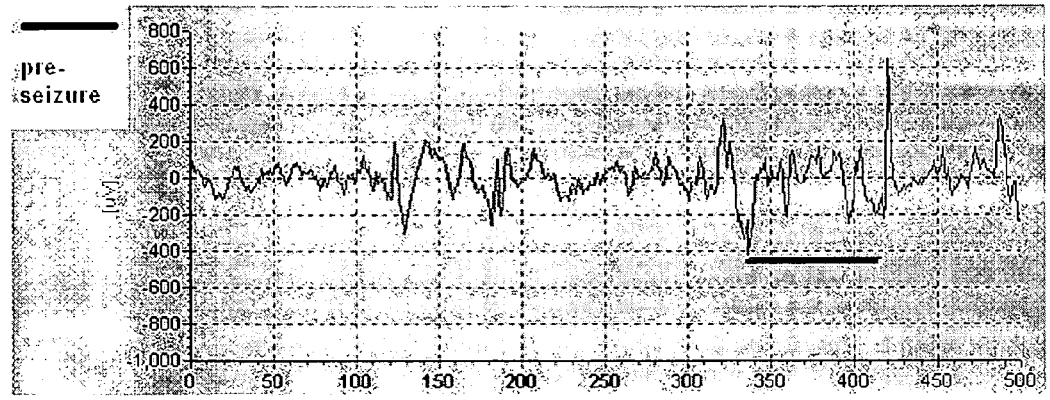
FIG. 7A shows EEG readings from a human subject indicative of pre-seizure activity as determined via the method according to the present invention.
Figure 7B:
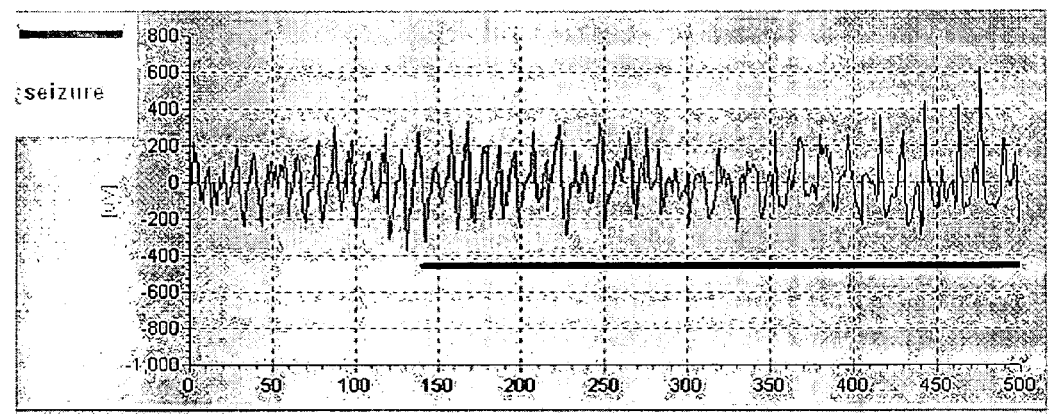
FIG. 7B shows EEG readings from a human subject indicative of seizure activity as determined via the method according to the method of the present invention.

FIG. 5 illustrates an exemplary method 400 used by the microcontroller 204 to detect the unique brain activity predictive of the imminent onset of epileptic seizures as illustrated in FIGS. 7A and 7B. Those skilled in the art will understand that the same method, after necessary modifications, may be used to monitor and treat other types of brain dysfunction. For example, the diffuse slowing of association of cortical EEG waves in patients with Alzheimer's disease or the localized slowing of EEG waves in patients with subarachnoid hemorage can be monitored with the method described herein and can be utilized to provide feed back on the efficacy of drugs delivered to treat these conditions avoiding toxic and ineffective drug deliveries to the dysfunctional areas of the cerebral cortex to slow the process of neuronal degeneration and facilitate neuronal repair. Generally, this method may be used to monitor all specific brain activity patterns that occur in diseases primarily associated with cerebral cortex dysfunction. The method 400 is vector-based and transforms detected brain activity into a stream of vectors. A vector is defined as a positive or a negative voltage change exceeding a pre-set threshold, allowing each vector to be described using two numbers that provide a direction and a magnitude to the vector. The main inter-vector relationships determined by the algorithm specifically tailored for detecting pre-seizure events and seizure onset as shown in FIG. 7A are: (1) magnitude change between two consecutive vectors, (2) similarity of directions of two or more consecutive vectors, (3) frequency of consecutive vectors with above-threshold magnitude and similar directions, and (4) number of vectors with above-threshold magnitude, similar directions, and above-threshold frequency within a prescribed period of time. The main inter-vector relationships are simultaneously determined for several differently band-passed data sets in a recording channel, allowing the comparison of multiple data sets within a single channel. Furthermore, this analysis is simultaneously performed for the signals of two or more recording channels allowing the determination of abnormal events in multiple cerebral cortical areas. Finally, the analysis sorts out the determined abnormal events into either of two categories: 1) those defining pre-seizure, or seizure predictive events; and 2) seizure onset events. This yields a two tier method that allows the system to respond with drug delivery to both pre-seizure events and seizure onset events. As the method 400 is able to recognize in real-time pre-seizure and seizure onset signals (e.g., as shown in FIGS. 7A and 7B, respectively) in the epileptic brain, the need for the use of calculations employing complex numbers is eliminated and a computationally inexpensive way to analyze relationships between consecutive vectors and recognize patterns characteristic of target abnormal brain activities is provided. This reduces the overall required complexity and power consumption of the microcontroller 204, which correspondingly decreases the required physical size of the microcontroller 204 and also provides longer periods between recharging of the power supply unit 206.

Although the method 400 is described with reference to a software program run by the microcontroller 204, the method 400 may also be implemented in hardware, or with a combination of hardware and software. Furthermore, those skilled in the art will recognize that as memory capactities and processor speeds increase, various less data efficient methods of detecting selected brain activities such as indicators of imminent epileptic seizures may become more desirable.

The method 400 begins by determining the magnitude of vectors corresponding to the sampled data (step 410). This may be accomplished, for example, by comparing voltages. The magnitude is directly proportional to an amplitude of the measured data and is compared to control data to determine if a vector's magnitude is above a first threshold value for the target brain activity (step 420). The first threshold value corresponding to the target brain activity may be predetermined or adjusted over time to tailor the method to the patient. The first threshold value and other relevant data, such as the sampling rate of the microcontroller 204 may be programmed into the microcontroller 204 prior to implantation or may be transmitted thereto via the telemetry unit 208 after implantation. If the magnitude is above the first threshold value, the direction of the vector is determined (step 430). Next, the frequency of the vector is determined (step 440) and compared to a second threshold value set based on control data for above-threshold vectors which may later be customized for the patient. If the frequency is above the second threshold value, the target brain activity is detected as occurring (step 450) and the microcontroller 204 signals that the target brain activity has been detected (step 460). The microcontroller 204 may then take any or all of the actions outlined above including supplying therapeutic agents to target areas of the brain. If however, neither the magnitude nor the frequency are above the first and second threshold values, respectively, the microcontroller 204 determines that no seizure is imminent and no action is taken.

Figure 6:
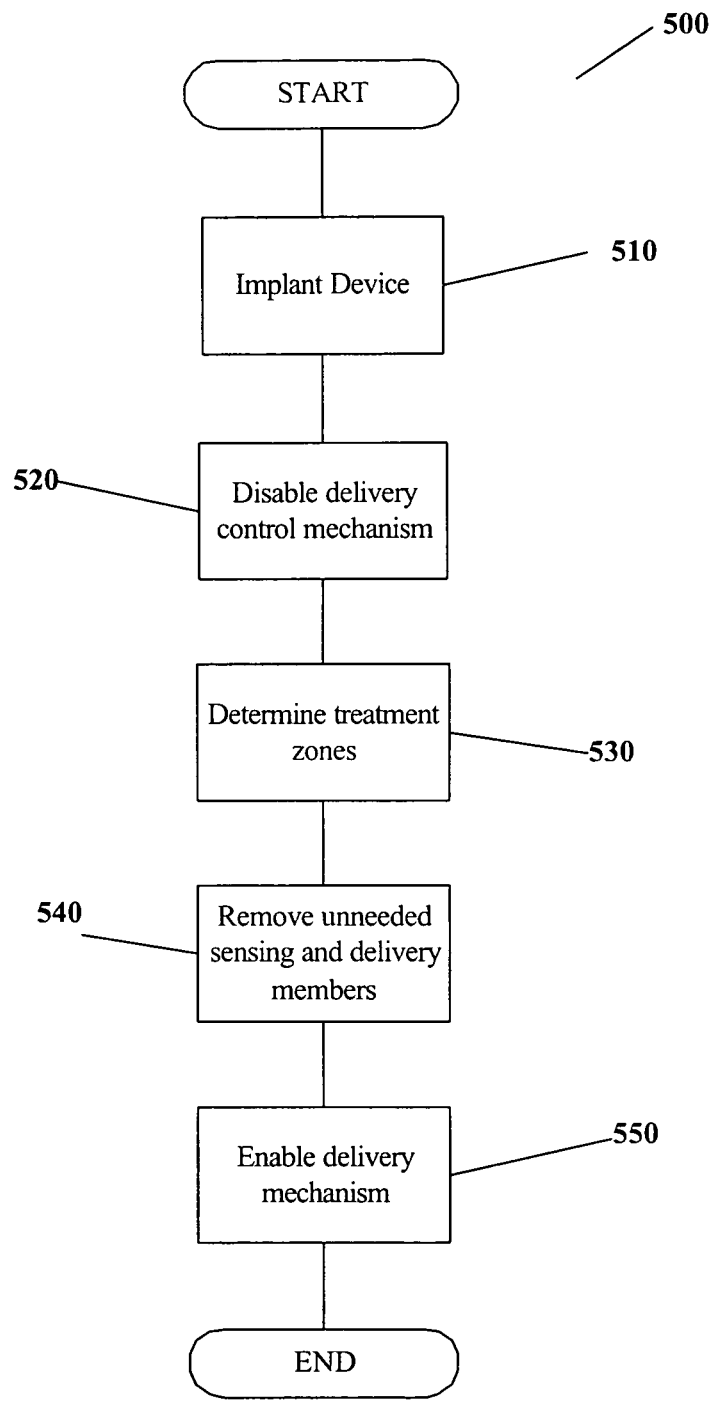
FIG. 6 shows an exemplary embodiment of a method for monitoring and diagnosing brain disorders according to the present invention.

The system according to the present invention may be used for diagnostic as well as treatment purposes. FIG. 6 shows an exemplary diagnostic method 500 according to the present invention. The system is first implanted as described above (step 510). The distal ends of the sensing and delivery members 100 may, for example, be implanted near areas suspected of or known to correspond to target brain activity. For diagnostic only applications, a delivery control mechanism of the control unit 200 may be disabled by either reprogramming the microcontroller 204 or by manual switching (e.g., disconnecting the bus 308) (step 520) to prevent the control unit 200 from activating the pump 302. Data received by the sensing devices 140 are sent to the control unit 200 through the bus 306, where the data is conditioned by the signal conditioner 202 before being transmitted by the telemetry unit 208 to an external recording device. A physician then determines which areas of the brain need treatment by analyzing the recorded data (step 530). Any sensing and delivery members 100 which are indicated by the data as unnecessary (i.e., which do not record target brain activity) may then be removed (step 540). Alternatively, the control unit 200 may be reprogrammed not to activate the pump 302 for the delivery of therapeutic fluids to the unnecessary sensing and delivery member 100. This allows the unneeded sensing and delivery members 100 to remain implanted serving only as sensing and/or mechanical supporting members. This avoids the physical trauma associated with surgical removal of the unnecessary sensing and delivery members 100 and allows continued monitoring of the untreated brain areas. Then if abnormal activity is later detected in the corresponding brain areas, they may be reactivated for the delivery of therapeutic fluids. In the final step, the delivery control mechanism is reenabled by reprogramming or switching (step 550).

Figure 8A:
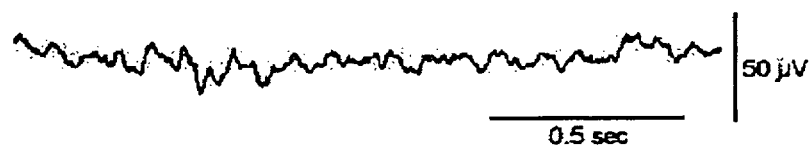
FIG. 8A shows EEG readings for a monkey before the administration into the cerebral cortex of an epileptogenic agent.
Figure 8B:
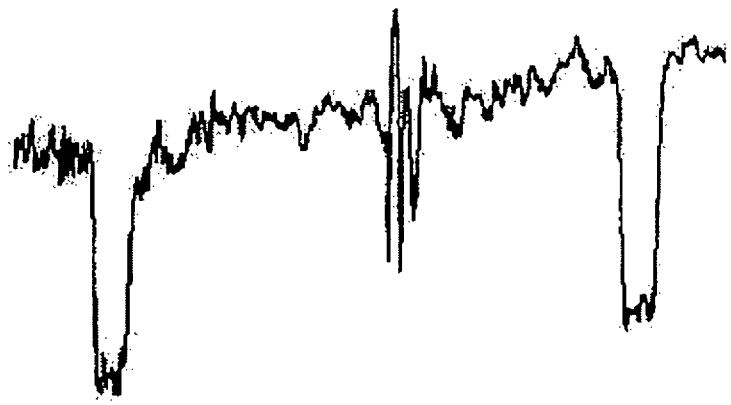
FIG. 8B shows EEG readings for the same monkey after the administered epileptogenic agent has taken effect.
Figure 8C:
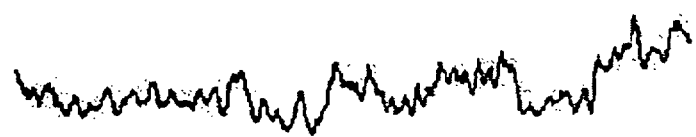
FIG. 8C shows EEG readings for the same monkey after delivery of an antiepileptic agent into the subdural space near the epileptogenic cortical area.

Although the present invention is designed ultimately for human use, its applicability should not be limited to use solely on human subjects. For example, the scope of the apparatus and methods of the present invention includes the use of the present invention in animals as a means to test the safety and effectiveness of therapeutic agents on the brain in conjunction with the system of the present invention. For example, as shown in FIGS. 8A-8C, EEG readings may be taken from monkeys in a manner similar to that described above for humans and, using an apparatus substantially the same as that described above, used to test the efficacy of therapeutic agents applied to the brain via the subdural space. As shown in FIG. 8A, base line cortical EEG activity for the test subject (e.g., a monkey) is recorded while none of the abnormal brain activity to be treated is present (e.g., before administering an agent designed to bring on a specific abnormal brain activity (e.g., an epileptogenic agent such as penicillin)). Brain activity is then measured until the specific abnormal activity is detected (e.g., seizure activity) and then the therapeutic agent to be tested (e.g., an antiepileptogenic agent) is supplied by the to target areas of the brain via sensing and delivery members 100 as described above and, using methods substantially similar to those described above, brain activity in the target areas is monitored to evaluate changes in the brain activity (i.e., the specific abnormal activity) and to determine the extent to which such changes are attributable to the therapeutic agent.

There are many modifications of the present invention which will be apparent to those skilled in the art without departing from the teaching of the present invention. The embodiments disclosed herein are for illustrative purposes only and are not intended to describe the bounds of the present invention which is to be limited only by the scope of the claims appended hereto.

What is claimed is:

1. A system for treating brain disorders, comprising:
   a first sensor for implantation at a first target area of the brain to detect data corresponding to target brain activity;
   an implantable processor analyzing data received from the first sensor to determine the presence of the target brain activity;
   a first fluid delivery member for implantation at a desired position in which a distal opening of the first fluid delivery member opens into a first predetermined portion of a subdural/subarachnoid space adjacent to the first target area;
   a first seal surrounding the first predetermined portion of the subdural/subarachnoid space and an exterior of the distal opening of the first fluid delivery member, the first seal configured so that in a sealing configuration, the first seal contacts tissue surrounding the first predetermined portion of the subdural/subarachnoid space to retain fluids delivered by the first fluid delivery member within the first predetermined portion of the subdural/subarachnoid space; and
   a controller analyzing data received from the first sensor and supplying a first therapeutic fluid to the first target area via the first fluid delivery member when the target brain activity is detected.

2. The system according to claim 1, wherein the first sensor is implanted within first predetermined portion of the subdural/subarachnoid space adjacent to the first target area of the brain.

3. The system according to claim 1, further comprising:
   a second sensor for implantation at a second target area of the brain to detect data corresponding to target brain activity; and
   a second fluid delivery member for implantation at a desired position in which a distal opening of the second fluid delivery member opens into a second predetermined portion of the subdural/subarachnoid space adjacent to the second target area, the processor analyzing data received from the first and second sensors and supplying one of the first therapeutic fluid and a second therapeutic fluid to the second target area via the second fluid delivery member when target brain activity is detected.

4. The system according to claim 3, further comprising a second seal surrounding the second predetermined portion of the subdural/subarachnoid space, the second seal configured so that in a sealing configuration, the second seal contacts tissue surrounding the second predetermined portion of the subdural/subarachnoid space to retain fluids delivered by the second fluid delivery member within the second predetermined portion of the subdural/subarachnoid space.

5. The system according to claim 4, wherein the second seal is movable between a disengaged configuration and the sealing configuration in which the second seal engages an inner surface of a dura mater and an outer surface of a cerebral cortex.

6. The system according to claim 5, in which the second seal is coupled to a source of inflation fluid via a second catheter, the second seal being moved to the sealing configuration by supplying fluid thereto.

7. The system according to claim 1, wherein the first sensor is a neurochemical sensor.

8. The system according to claim 1, further comprising a fluid reservoir implanted remote from the brain.

9. The system according to claim 1, wherein the first fluid delivery member includes at least one distal opening having a plurality of perforations defining an active area of the first fluid delivery member.

10. The system according to claim 1, wherein processor utilizes a vector-based signal analysis to converting the detected brain activity into a series of vectors, the processor analyzes a magnitude and a direction of individual vectors and the processor analyzes a frequency of a plurality of target vectors related by at least one of magnitude and direction.

11. The system according to claim 1, further comprising a telemetry system communicating data to an external output device.

12. The system according to claim 11, wherein the data communicated to an external device includes results of the detection and analysis of brain activity.

13. The system according to claim 11, wherein the data communicated to an external device includes one of EEG signals, status related to an operational status of the system, and programming updates.

14. The system according to claim 1, further comprising an implanted pump supplying to the first fluid delivery member a cleansing fluid for flushing the first fluid delivery member.

15. The system according to claim 14, wherein the implanted pump supplies the first therapeutic agent and the cleansing fluid to the first fluid delivery member.

16. The system according to claim 14, wherein the pump includes a plurality of chambers, a first one of the chambers including a neutral fluid for inflating the first seal.

17. The system according to claim 16, wherein a second one of the chambers is a reservoir for receiving fluid withdrawn from the subdural/subarachnoid space and a third one of the chambers includes a therapeutic agent for introduction into the subdural/subarachnoid space.

18. The system according to claim 16, wherein a third one of the chambers includes a fluid for cleansing the fluid delivery member.

19. The system according to claim 1, wherein the processor includes a first device selected from the group consisting of a microprocessor, a digital signal processor, a programmable logic array, a programmable logic device, a field programmable device and an application specific integrated circuit.

20. The system according to claim 19, wherein the processor includes a second device selected from the group.

21. The system according to claim 20, wherein the first and second devices are same types of devices.

22. The system according to claim 20, wherein the first and second devices are different types of devices.

23. The system according to claim 1, wherein the first seal is movable between the sealing configuration in which the first seal engages an inner surface of a dura mater and an outer surface of a cerebral cortex and a disengaged configuration in which fluid flow is permitted between the first predetermined portion of the subdural/subarachnoid space and portions of the subdural/subarachnoid space outside of the first predetermined portion.

24. The system according to claim 23, in which the first seal is coupled to a source of inflation fluid via a first catheter, the first seal being moved to the sealing configuration by supplying fluid thereto.

25. The system according to claim 1, wherein the fluid delivery member comprises one of a microperforated segment and a disk shaped distal end including microperforations formed therein.

26. The system according to claim 1, wherein the first seal contacts an inner surface of a dura mater and an outer surface of a cerebral cortex.

27. A system for treating brain disorders, comprising:
a first sensor for implantation at a first target area of the brain to detect data corresponding to target brain activity;
an implantable processor analyzing data received from the first sensor to determine the presence of the target brain activity;
a first fluid delivery member configured for implantation at a desired position in which a distal opening of the first fluid delivery member opens into a first predetermined portion of a subdural/subarachnoid space adjacent to the first target area, the distal opening of the first fluid delivery member including a plurality of perforations defining an active area of the first fluid delivery member which, when implanted in the desired position, are located within the first predetermined portion of the subdural/subarachnoid space;
a first seal surrounding the first predetermined portion of the subdural/subarachnoid space and an exterior of the distal opening of the first fluid delivery member, the first seal configured so that in a sealing configuration, the first seal contacts an inner surface of a dura mater and an outer surface of a cerebral cortex to retain fluids delivered by the first fluid delivery member within the first predetermined portion of the subdural/subarachnoid space; and
a controller analyzing data received from the first sensor and supplying a first therapeutic fluid to the first target area via the first fluid delivery member when the target brain activity is detected.

\* \* \* \* \*